United States Patent
Cha et al.

(10) Patent No.: US 8,075,492 B2
(45) Date of Patent: Dec. 13, 2011

(54) AUTOMATIC DECOMPRESSION VALVE FOR SPHYGMOMANOMETER WITH EXTENSION SPRING

(75) Inventors: Un Jong Cha, CheongJu (KR); Kyung Ah Kim, CheongJu (KR); In-Kwang Lee, Geosan-Gun (KR)

(73) Assignee: Un Jong Cha, Cheongju (KR)

( * ) Notice: Subject to any disclaimer, the term of this patent is extended or adjusted under 35 U.S.C. 154(b) by 1397 days.

(21) Appl. No.: 11/611,325

(22) Filed: Dec. 15, 2006

(65) Prior Publication Data
US 2008/0027335 A1   Jan. 31, 2008

(30) Foreign Application Priority Data
Jul. 26, 2006  (KR) .................. 10-2006-0070411

(51) Int. Cl.
*A61B 5/02* (2006.01)

(52) U.S. Cl. ...................................... 600/498; 600/485

(58) Field of Classification Search .................. 600/498
See application file for complete search history.

(56) References Cited

U.S. PATENT DOCUMENTS

| | | | | | |
|---|---|---|---|---|---|
| 3,918,437 | A | * | 11/1975 | Saba | 600/498 |
| 4,200,259 | A | * | 4/1980 | Ueda | 251/285 |
| 5,323,806 | A | * | 6/1994 | Watari et al. | 137/504 |
| 6,635,020 | B2 | * | 10/2003 | Tripp et al. | 600/488 |
| 2007/0060825 | A1 | * | 3/2007 | Newman et al. | 600/498 |
| 2007/0060826 | A1 | * | 3/2007 | Krauter | 600/498 |

FOREIGN PATENT DOCUMENTS

KR  10-0619242  8/2006

OTHER PUBLICATIONS

English language abstract of KR 100619242.

* cited by examiner

*Primary Examiner* — Patricia Mallari

(57) ABSTRACT

Disclosed is an automatic decompression valve for sphygmomanometer with an extension spring, which can decompress pressure at a constant without control of the decompression vale of the sphygmomanometer, and be used uprightly regardless of a peripheral circumstance. The automatic decompression valve includes: a valve body having an inlet through which air is introduced from a cuff therein, and an outlet through which the introduced air is exhausted; a piston having a piston shaft for moving toward the outlet in the valve body; a spring having one end connected to the piston; a three-way valve provided with a connector with which the valve body is assembled, and air inlet and outlet, the three-way valve being connected to the other end of the spring; and a support for supporting the three-way valve.

8 Claims, 5 Drawing Sheets

AUTOMATIC DECOMPRESSION VALVE FOR SPHYGMOMANOMETER WITH EXTENSION SPRING

TECHNICAL FIELD

The present invention relates to a blood pressure measuring apparatus, and more particularly to an automatic decompression valve for a sphygmomanometer with an extension spring, which can decompress in the sphygmomanometer without direct operation by a user, and maintain its vertical position regardless of a slope of the bottom surface of the sphygmomanometer.

BACKGROUND ART

In general, blood pressure in an artery periodically increases and decreases depending on systole and diastole of the heart. In the periodic change of the blood pressure, the maximum of the blood pressure is referred to as systolic pressure $P_{SYS}$, and the minimum of the blood pressure is referred to as diastolic pressure $P_{DIAS}$. Typically, the blood pressure is indicated by $P_{SYS}/P_{DIAS}$, and its measurement unit is mmHg.

A method of measuring blood pressure employs the principle of non-invasive blood pressure measurement. In this principle, a part of an arm is pressed by an oppressing pressure. At this time, the oppressing pressure is indicated by $P_C$, and the blood pressure in arteries distributed in the arm is shown by BP. The principle is such that as tissue around the arteries transfers the oppressing pressure $P_C$ into the blood pressure BP, the arteries are closed or opened according to the oppressing pressure $P_C$ and the blood pressure BP.

If the oppressing pressure $P_C$ is greater than the blood pressure BP, the arteries are closed. To the contrary, if the oppressing pressure $P_C$ is less than the blood pressure BP, the arteries remain opened. Hence, if the oppressing pressure $P_C$ sufficiently increases, i.e. $P_C>P_{sys}$, all the arteries are closed. On the other hand, when the oppressing pressure $P_C$ on the arm decreases, the arteries, which have been closed, are somewhat opened, and thereby it is possible at a position on the arm to ausculate heart rate and blood vortex flowing through the narrow arteries. This is called the Korotkoff Sound.

After hearing the Korotkoff Sound, the oppressed pressure further decreases to allow the arteries to fully open. That is, if the oppressing pressure $P_C$ becomes less than the diastolic pressure $P_{DIAS}$, the Korotkoff Sound disappears.

According to the principle of the non-invasive blood pressure measurement, the oppressing pressure $P_C$ at a point of a time of hearing the Korotkoff Sound is recorded as the systolic pressure $P_{SYS}$, and the oppressing pressure $P_C$ at a point of a time when the Korotkoff Sound disappears is recorded as the diastolic pressure $P_{DIAS}$.

A mercury sphygmomanometer is one device that uses the principle of the non-invasive blood pressure measurement as described above. The conventional mercury sphygmomanometer includes a blood pressure cuff which is wound on a users arm and filled with air to generate pressure enabling the cuff to oppress the users arm, a mercury column for indicating the pressure $P_C$ in the cuff (it indicates the pressure mmHg by its height), a bulb shaped air injector for injecting air into the cuff with a users hand so as to increase the pressure in the cuff, and a decompression valve for controlling a decompression rate by releasing a screw with the users hand.

As shown in FIG. 1 in the mercury sphygmomanometer, the air injector 10 has a rubber-made ball shape with one side connected to the cuff 20 and the other side communicated with atmosphere A. The air injector 10 has one-way valves 11 and 11' mounted on a side connected to the cuff 20 and the other side communicated with the atmosphere A, respectively. A decompression valve 30 is installed near the one-way valve 11 connected to the cuff 200. Therefore, when the decompression valve 30 is fully closed and the air injector 10 is pressed in a direction marked by an arrow M in FIG. 1, the inner pressure in the air injector 10 increases. Thus, the inner pressure of the air injector 10 causes the atmosphere-sided one-way valve 11' to be closed and the cuff-sided one-way valve 11 to be opened, so that the air in the air injector 10 is injected into the cuff 20 in a direction marked arrows in FIG. 1. When the pressure applied to the air injector 10 is released, the air injector is relaxed by its elasticity. In other words, the air injector 10 expands outward in a direction marked by the arrow M to generate negative pressure therein, so that the cuff-sided one-way valve 11 is closed and the atmosphere-sided one-way valve 11' is opened. Hence, the exterior air is introduced into the air injector 10. These processes repeat and generate high pressure in the cuff 20.

When the decompression valve 30 is opened to decrease the pressure in the cuff 20 in order to measure the user blood pressure, the air is discharged from the cuff 20 so that the pressure drops in the cuff 20. However, since the decompression valve 30 has a configuration in the form of a screw, there is required skill in controlling a decompression rate using the decompression valve because of the sensitivity of the decompression valve.

It a user intends to measure his/her blood pressure using a mercury sphygmomanometer, the cuff 20 is wound on his/her arm and then the decompression valve 30 is completely closed. Next, when air is injected into the cuff 20 through the air injector 10 so that the pressure $P_C$ in the cuff 20 is greatly higher than the systolic pressure $P_{SYS}$, as described above, the pressure of the mercury sphygmomanometer 40 connected to the cuff 20 increases. After the air is introduced into the cuff 20 so that the oppressing pressure $P_C$ increases to be sufficiently higher than the systolic pressure $P_{SYS}$, the decompression valve 30 is somewhat opened to slowly decompress the oppressing pressure $P_C$ at a rate of −3~5 mmHg/sec which is a recommended decompression rate. At this time, the user instantly reads the height of the mercury column 40 at a time point of hearing the Korotkoff Sound through a stethoscope, so as to determine the systolic pressure $P_{SYS}$, and continues to decompress the oppressing pressure $P_C$. Further, the user reads the height of the mercury column at a time point when the Korotkoff Sound completely disappears and determines the diastolic pressure $P_{DIAS}$.

However, there is required sufficient skill in measuring the blood pressure using the conventional mercury sphygmomanometer because the user has to determine the time points when the Korotkoff Sound occurs and disappears by listening for the Korotkoff Sound with his/her ears using the stethoscope, instantly read the height of the mercury column at those time points with his/her eyes, and control the decompression rate to be −3~−5 mmHg/sec with his/her hand.

On the other hand, in the case of not the mercury sphygmomanometer but an automatic sphygmomanometer, a computer automatically controls a small air pump or valve to maintain a constant decompression rate However, this requires very complicated and accurate control algorithms.

Therefore, if the regulation of the decompression valve is completed, motive power for air outflow increases with the pressure $P_C$ in the cuff 20, as seen in the graph of FIG. 3. As a result, air outflow velocity increases while the decompression rate also increases. On the other hand, when the pressure $P_C$ decreases, the motive power for the air flow is reduced, resulting in decreasing the decompression rate. In other words, the pressure $P_C$ decreases not linearly but exponentially. FIG. 3 is a graph illustrating a decompression rate in proportion with a time in the conventional mercury sphygmomanometer under a condition of a constant pressure $P_C$ according to the opening and closing of the decompression valve. It is understood that the decompression rate is generally changed according to the opening and closing of the decompression valve, but the pressure $P_C$ is exponentially decompressed.

The operation of the decompression valve 30 shown in FIG. 1 is described as follows:

As the air is discharged from the cuff 20 through the decompression valve 30 by the pressure $P_C$ which is higher than the atmospheric pressure, the pressure $P_C$ drops. The decompression rate u of the pressure $P_C$, i.e. variation of the pressure $P_C$ per unit time ($dP_C/dt$) is in proportion to the air outflow Q, and can be expressed by a following equation;

$$u = dP_C/dt \propto Q,$$

wherein since the air outflow Q can decrease as the fluid resistance R of the decompression valve 30 increases, the air outflow Q is in inverse proportion to the fluid resistance R. This can be expressed by a flowing equation:

$$u = dP_C/dt \propto Q \propto 1/R$$

Therefore, the decompression rate is in inverse proportion to the fluid resistance. This can be expressed by a following equation:

$$\frac{dP_C}{dt} \propto \frac{1}{R}$$

Meanwhile, when the pressure $P_C$ which is a motive power for the air outflow, increases, the decompression rate is in proportion to the pressure $P_C$. The decompression rate of the pressure $P_C$ is in proportion to the pressure $P_C$, and in inverse proportion to the fluid resistance R, as expressed by a following equation:

$$\frac{dP_C}{dt} \propto \frac{P_C}{R}$$

Here, if the fluid resistance R is constant, i.e. the extent of opening and closing of the decompression valve can be constantly maintained, the decompression rate $dP_C/dt$ is in proportion to only $P_C$. Therefore, when the pressure $P_C$ increases, the decompression rate also accelerates. Further, when the pressure $P_C$ drops, the decompression rate drops. Thus, the variation of the pressure $P_C$ according to time is in the form of exponential function, as shown in FIG. 3.

As described above, if the proper decompression rate of about −3~−5 mmHg/sec required to measure the blood pressure is maintained regardless of the pressure $P_C$, the fluid resistance R must be in proportion to the pressure $P_C$. That is, if the fluid resistance R is changed in proportion to the pressure $P_C$, the equation can be expressed as follows:

$$R = \frac{P_C}{k},$$

wherein k is constant.

If R in the foregoing equation is substituted with this equation, a following equation can be obtained:

$$\frac{dP_C}{dt} \propto \frac{P_C}{\frac{P_C}{k}}$$

wherein k is constant. Thus, the decompression rate becomes constant, and the pressure $P_C$ linearly decreases.

Based on the above-mentioned principle, the applicant has filed a Korean Patent Application Serial No. 2005-0042317, entitled with "Pressure-Linked Automatic Decompression Valve for Sphygmomanometer", in which the decompression valve makes a fluid resistance R to be in proportion to pressure $P_C$ using the elasticity of a spring so as to linearly decompresses the pressure. As shown in FIG. 4A, according to the Korean patent application, the pressure-linked automatic decompression valve 100 is used in an upright position, and has an outer cylinder 112 and a piston shaft 115. The decompression valve 100 has an overlapping region defined by the movement of the piston shaft 115 in the outer cylinder 112 and having a predetermined length L. Further, the decompression valve 100 is connected at a lower portion thereof to the connector of the sphygmomanometer so that the pressure $P_C$ of the cuff is applied to a piston 114.

In the Korean Patent Application, when air is injected into the cuff, the pressure $P_C$ increases to push the piston 114. Thus, the piston shaft 115 moves upward to maximize the overlapping length L. At this time, a compression spring 116 interposed between the piston 114 and an inner cylinder is compressed to the maximum extent. When the air injection is interrupted, the air is discharged from the cuff through a gap between the outer cylinder 112 and the piston 114, and the overlapping region with the predetermined length L. At this time, the gap between the piston 114 and the outer cylinder 112 is sufficiently enlarged while the thickness of the piston is made narrow, so that the air can pass by the piston 114 without being subject to resistance. However, a gap between the piston shaft 115 and the outer cylinder is made very narrow to cause fluid resistance. Since the width of the gap is constant, the fluid resistance is in proportion to the overlapping length L. In other words, if the overlapping length L increases, the fluid resistance also increased to prevent the air outflow. As the pressure $P_C$ increases at an initial time when the air outflow starts, a motive power for the air outflow grows. The air outflow rate to the constant fluid resistance is rapid. However, since the overlapping length L also extends, the fluid resistance increases to reduce the air outflow rate. The pressure $P_C$ and the overlapping length L operate in opposite directions.

In addition, when the pressure $P_C$ drops as the air outflow proceeds, force to compress the spring 116 is reduced. As a result, the spring 116 returns to an initial position, and thereby the overlapping length L further becomes shorter. The decreasing of the pressure $P_C$ means that the motive power for the air outflow is reduced. Meanwhile, the reduction of the overlapping length L means that the fluid resistance decreases. Even though the motive power decreases to decelerate the air outflow rate, the fluid resistance is lowered along with the deceleration of the air outflow rate, thereby offsetting the air outflow rate caused by the reduction of the motive power. That is, as the fluid resistance R is reduced in proportion to the reduction of the pressure $P_C$ which is the motive power for the air outflow, it is possible to obtain the constant air outflow rate regardless of the pressure $P_C$. Thus, the pressure $P_C$ can be linearly decompressed at a constant rate.

In the decompressing process as described above, predetermined friction $F_f$ is generated during the movement of the piston 114 and the piston shaft 115, and the compression and extension of the spring. When the instrument is in an upright position, the weight $W_n$ of the piston 114 and the piston shaft 115 can offset an upward friction caused by the downward movement of the piston 115 and the piston shaft 114, so that the decompression valve can perform an ideal operation.

The pressure-linked automatic decompression valve 100 as described above operates based on the principle in which the compressed length of the spring 116, which is the overlapping length L, extends to be in proportion to the pressure $P_C$ and the fluid resistance R of the valve.

However, the spring 116 tends to be compressed and deviated in not only a vertical direction but also a horizontal direction (see FIG. 4B). Therefore, the spring unnecessarily frictionizes the outer cylinder 112 as shown in FIGS. 4A and 4B.

As shown in FIG. 4B in which a part of the spring 116 of FIG. 4a is shown, since the spring 116 is subjected to a vertical pressure P upward and downward, the spring 116 tries to horizontally deviate across the criteria point S. As the horizontal deviation of the spring 116 is irregularly generated, the friction between the spring 116 and an inner surface of the outer cylinder 112 irregularly occurs. Thus, it is impossible to offset the friction by using the weight of the valve. This causes the valve 100 not to operate smoothly. Further, the valve 100 according to the Patent Application must be used in an upright position. However, in some cases, the valve 100 cannot be positioned uprightly under the circumstance of measuring the blood pressure. Therefore, there is required a solution in which the valve 100 is maintained to be upright regardless of the slope of a floor on which the valve is located.

DISCLOSURE OF THE INVENTION

Therefore, the present invention has been made in view of the above-mentioned problems, and it is an object of the present invention to provide an automatic decompression valve for a sphygmomanometer using an extension spring, which can automatically and constantly decompress pressure in a blood pressure cuff without control of a decompression valve manually or by an electric motor in the sphygmomanometer, and prevent a friction due to the deviation of the spring.

According to an aspect of the present invention, there is provided an automatic decompression valve for a sphygmomanometer using an extension spring, which includes: a valve body having an inlet through which air is introduced from a cuff therein, and an outlet through which the introduced air is exhausted; a piston having a diameter smaller than an inner diameter of the cylinder and provided with a piston shaft which moves upward and downward in the outlet of the valve body; a spring having one end connected to a lower surface of the piston; a three-way valve provided with a connector with which the valve body is assembled, and air inlet and outlet, and connected to the other end of the spring; and a support for supporting the three-way valve.

The cylinder of the valve body has a seating jaw formed at an intermediate portion thereof, on which the piston is seated. Further, the valve body has a protrusion at an upper portion thereof, which extends into the valve body and has an air exhaust hole formed through the protrusion so that the piston shaft moves in the air exhaust hole. The cylinder of the valve body partially overlaps with the protrusion.

Preferably, the spring is connected at one end thereof to the piston shaft extending downward through the piston, and at the other end to the valve body of the three-way valve by a thin plate which is folded and inserted into the connector of the three-way valve.

Preferably, the sprint includes an extension spring.

Further, the three-way valve is mounted on a valve support on which valve supporting members are formed. The three-way valve is rotatably supported by the valve support. In addition, the support has a pedestal mounted on a lower portion thereof.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Hereinafter, the preferred embodiments of the present invention will be described in detail with reference to the accompanying drawings.

Figure 5:
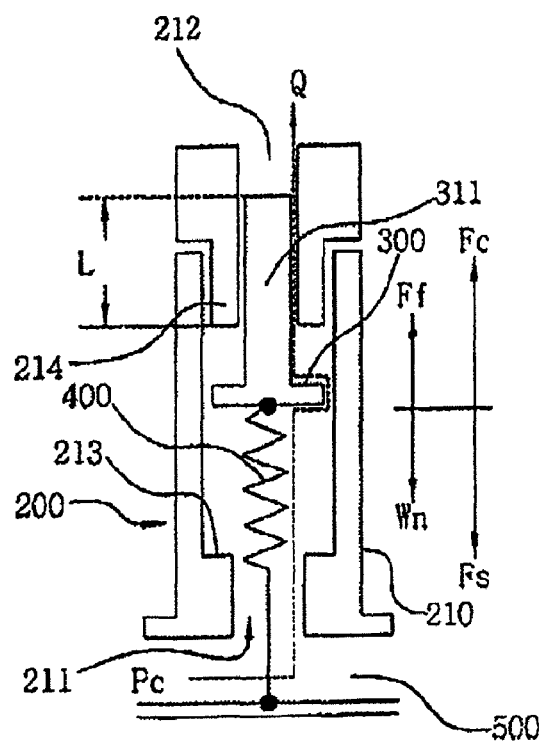
FIG. 5 is a schematic view showing a decompression valve for a sphygmomanometer according to the present invention.

FIG. 5 is a schematic view showing a valve body 200 used in a decompression valve for a sphygmomanometer according to the present invention.

Figure 1:
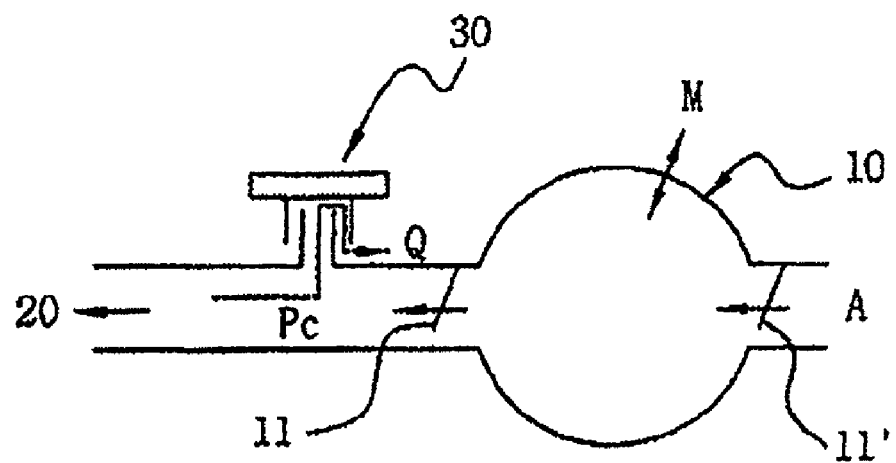
FIG. 1 is a schematic view showing a decompression valve and an air injector of a conventional mercury sphygmomanometer.

In FIG. 5, the valve body 200 of the present invention has a cylinder 210 formed with an inlet 211 through which air $P_C$ is introduced from a cuff (not shown, see FIG. 1) into the cylinder 210, and an outlet 212 through which the air is exhausted. The cylinder 210 has a seating jaw 213 formed at a lower portion or an intermediate portion thereof. A piston 300 with a piston shaft 311 is inserted in the cylinder 210 and may be seated on the seating jaw 213. The piston shaft 311 has a diameter smaller than the inner diameter of the outlet 212, and can move along the outlet 212. The piston 300 has a lower surface to which a spring 400 is connected. The spring 400 is easily connected to the piston 300 in such a manner that one end of the spring 400 is inserted into a hole formed in an end of the piston shaft 311 which extends through the piston 300 below the lower surface.

Further, the valve body 200 includes a protrusion 214 having a diameter smaller than an inner diameter of the valve body 200, which is fitted to the outlet 212 of the valve body 200. The protrusion 214 has an overlapping Length in which the piston shaft 311 overlaps with the protrusion 214.

Figure 6:
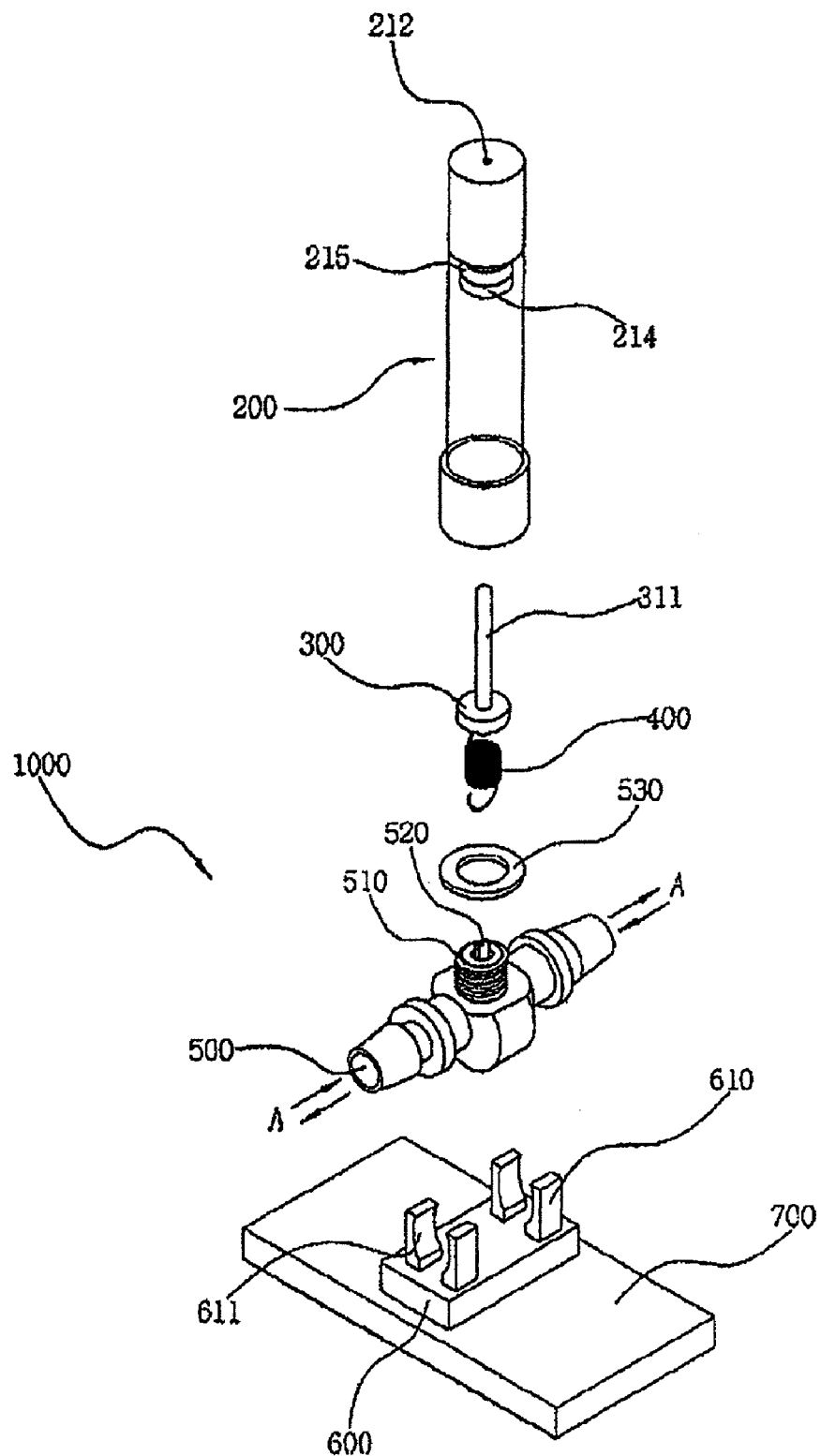
FIG. 6 s an exploded perspective view showing the decompression valve for the sphygmomanometer according to the present invention.

FIG. 6 is an exploded perspective view of the automatic decompression valve 1000 for the sphygmomanometer according to the present invention. The decompression valve 100 of the present invention includes the valve body 200, the piston 300 having the piston shaft 311 which is inserted into the valve body 200, the extension spring 400 connected to the lower surface of the piston 300, a three-way valve 500 into which the valve body 200 is inserted, a support 600 for supporting the three-way valve 500, and a pedestal 700 for supporting the support 600.

When the protrusion 214 is assembled with the valve body 200 as described above, an O-ring 215 is disposed between the protrusion 314 and the valve body 200 so as to maintain an air-tight seal.

In addition, the extension spring 400 has one end connected to the lower surface of the piston 300, and the other end connected to a thin plate 520 in the connector 510 of the valve body 200 of the three-way valve 500. At that time, the other end of the spring 400 is connected to the thin plate 520 in such a manner that the thin plate 520 is folded and the other end is inserted into the thin plate 520. The thin plate 520 to which the spring 540 is connected is fitted to the connector 510 in parallel with airflow A in the three-way valve 500. Alternatively, a connecting wire may be arranged across the connector 510 and then the other end of the spring 400 may be connected to the connecting wire.

The valve body 200 can be screw assembled with the connector 510 of the three-way valve 500 as described above. At this time, the O-ring 530 is interposed between the connector 510 and the valve body 200 to prevent the inflow and outflow of the air.

The valve body 200 and the three-way valve 500 which have the spring 400 and the connector 400, respectively, are supported by the support 600 with the supporting members 610 defining the reception space 611. In this case, the reception space 611 has a diameter R to allow the three-way valve 500 to rotate by force, which is a little smaller than that of the three-way valve 500. It is prefer to prevent the three-way valve 500 from rotating by itself after the three-way valve is disposed in the reception space 611.

Further, the pedestal 700 is installed under the support 600 to support the depression valve 1000. In this case, the pedestal 700 is preferably formed from a material which is heavier than the support 600 in order to provide a pedestal effect. Of course, the pedestal 700 and the support 600 may be integrally formed.

Hereinafter, the operation of the automatic depression valve for the sphygmomanometer using the extension spring according to the present invention will be described.

Figure 2:
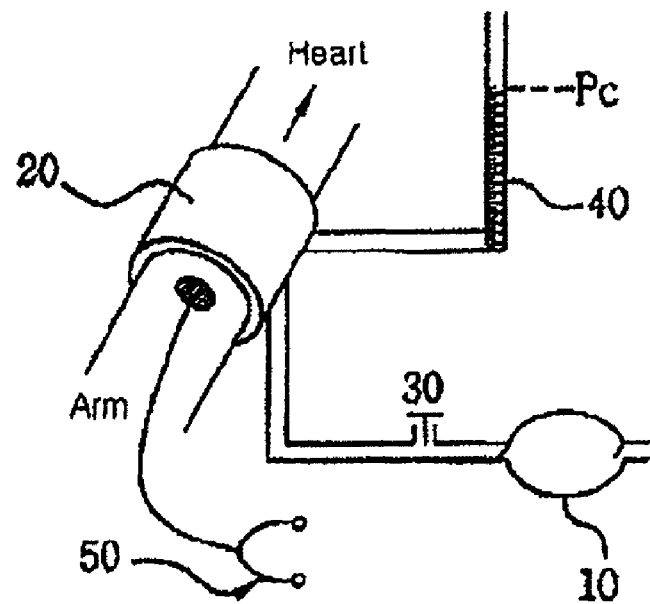
FIG. 2 is a view showing a configuration of the conventional mercury sphygmomanometer.
Figure 3:
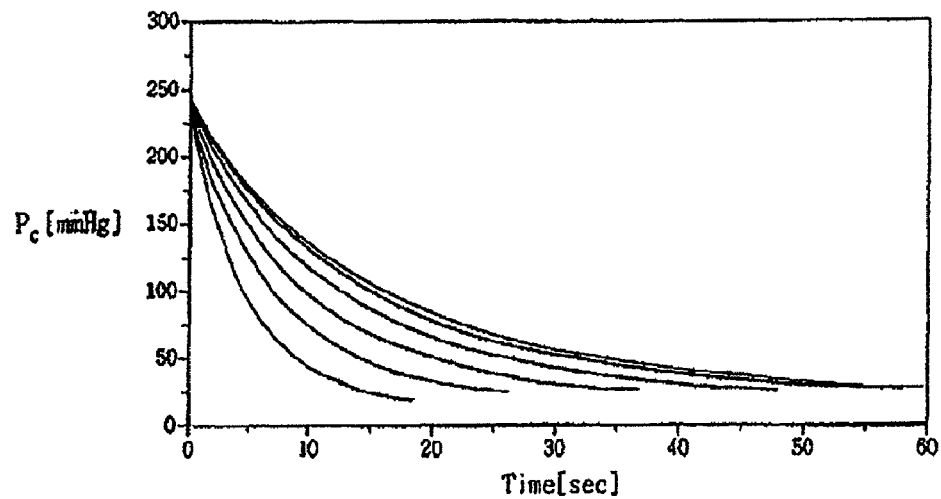
FIG. 3 is a graph illustrating a decompression rate in proportion wish a time in the conventional mercury sphygmomanometer.
Figure 4A:
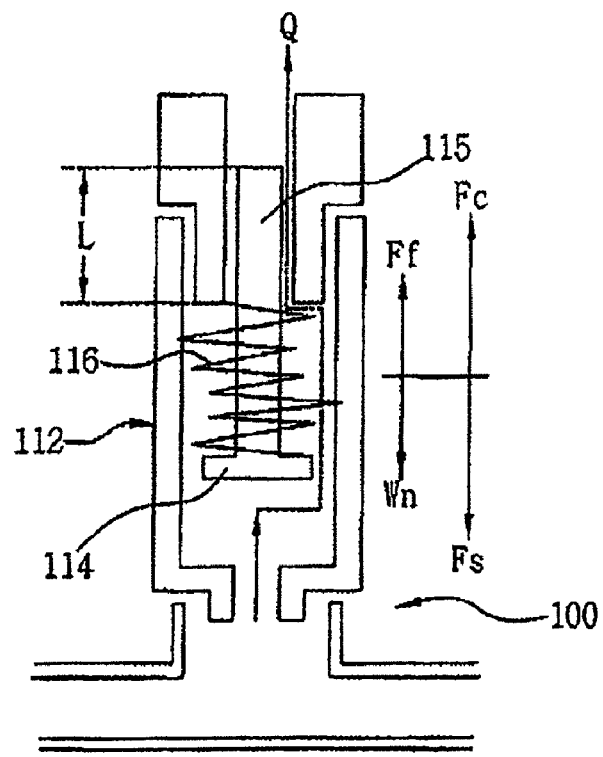
FIG. 4A is a schematic view showing a decompression apparatus or a conventional sphygmomanometer.
Figure 4B:
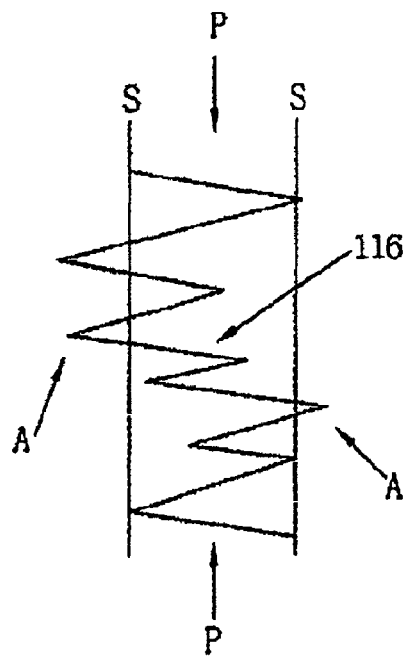
FIG. 4B is a partial enlarged view of the decompression apparatus of FIG. 4A.

With use of the present invention, first the elements constituting the sphygmomanometer are assembled. In other words, an air injection tube connected to the cuff is coupled to one port of the three-way valve 500 (for example, the left-side port in FIGS. 6 and 7), and an air injection tube connected to the air injector 10 (see FIGS. 1 and 2) is assembled with the other port of the three-way valve 500. Next, the air is injected from the air injector 10 to the cuff.

The decompression valve 1000 of the present invention is mounted on the sphygmomanometer, instead of the conventional decompression valve 30. Since the decompression valve 1000 is made to have a decompression rate of −3~−5 mmHg/sec, an amount of air which leaks out of the decompression valve 1000 is smaller than the amount of air introduced from the air injector 10 to the cuff 20 and can cause the existence of the leaking air to go unnoticed. Therefore, the air can be injected from the air injector 10 to the cuff 20 so that the pressure $P_C$ in the cuff 20 is sufficiently higher than the systolic pressure $P_{SYS}$ without treatment to the decompression valve 1000.

Next, the user merely reads the height of the mercury column at a time point of hearing the Korotkoff Sound through the stethoscope 50 and at a time point when the Korotkoff Sound disappears without the regulation of the decompression valve 30, thereby determining the systolic pressure $P_{SYS}$ and the diastolic pressure $P_{DIAS}$. At this time, the cuff pressure $P_C$ introduced from the cuff 20 is discharged through the outlet 212 along a dotted line arrow in FIG. 5. Further, as the decompression valve 1000 of the present invention is upright, the friction $F_f$ between the piston 300 and the cylinder can be offset by the weight $W_n$ of the piston 300 which is due to gravity. When the spring 400 is elongated, its diameter is reduced. Thus, the extension spring 400 does not fractionize the valve body so as to gain ideal changes. This is different from the conventional compression spring.

The length L in which the piston 300 overlaps with the upper jaw of the cylinder 210 of the valve body 200, can be changed according to the magnitude of the cuff pressure $P_C$. Here, the spring 400 is elongated when the cuff pressure $P_C$ increases, so that the overlapping length L extends. To the contrary, when the cuff pressure $P_C$ decreases, the pressure of the air flowing form the cuff becomes small. Therefore, the piston 300 moves downward while the spring is constricted. As a result, the overlapping length L becomes short. Since the diameter of the spring is reduced when the spring 400 is elongated, the spring 400 does not contact with the valve body so that the friction does occur between the valve body and the spring 400. Thus, the change of ideal fluid resistance can be gained. This is a difference from the conventional compression spring.

As shown in FIG. 5, when the extension spring 400 is elongated in proportion with the increasing of the cuff pressure $P_C$ so that the overlapping length L extends, the fluid resistance increases in proportion with the extension of the length L. Accordingly, the pressure of the exhausted air increases, but the amount of the exhausted air is reduced as the air passes through the region in which the piston overlaps with the protrusion. Therefore, the amount of the exhausted air is constant due to the balance between the pressure and the fluid resistance. When the discharge of the air causes the cuff pressure $P_C$ to be lowered so that the overlapping length L is more and more short, the fluid resistance is reduced. As a result, the pressure of the exhausted air somewhat increases. However, since the overlapping length also becomes short, the amount of the exhausted air can be maintained to be constant. In other words, as the fluid resistance can be automatically changed depending on the extension of the spring 400 caused by the pressure $P_C$ of the cuff, the amount of the exhausted air can be generally maintained to be constant. It is understood that this is because the fluid resistance is in proportion with the overlapping length.

Further, the compression valve 1000 of the present invention is preferably used uprightly. This is to offset the friction $F_f$ occurring between the piston 300 and the cylinder 210 by the gravity of the piston 300. Otherwise, the friction $F_f$ causes the air not to be constantly discharged from the cylinder.

As described above, when the systolic pressure $P_{SYS}$ and the diastolic pressure $P_{DIAS}$ are determined, the cuff 20 is removed from the users arm. The removed cuff 20 remains in itself so that the pressure therein can decrease naturally through the valve body 200. Further, a connector of the air injector 10 is released from the cuff 200 so that the air in tie cuff 20 is exhausted outside.

Further, according to the present invention, even though the valve body 200 cannot be upright during the measurement of the blood pressure, the three-way valve 500 on which the valve body 200 is mounted can rotate by force in the receiving space 610 of the support 600.

Figure 7:
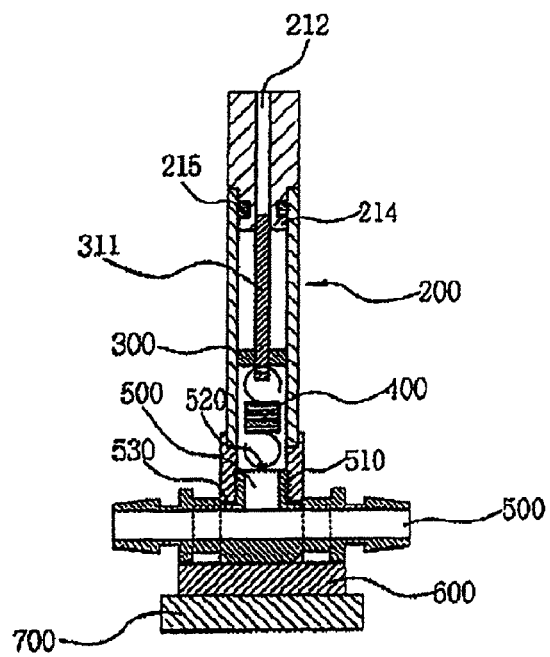
FIG. 7 is a sectional view showing the decompression valve for the sphygmomanometer according to the present invention, in which parts of the decompression valve are assembled.
Figure 8:
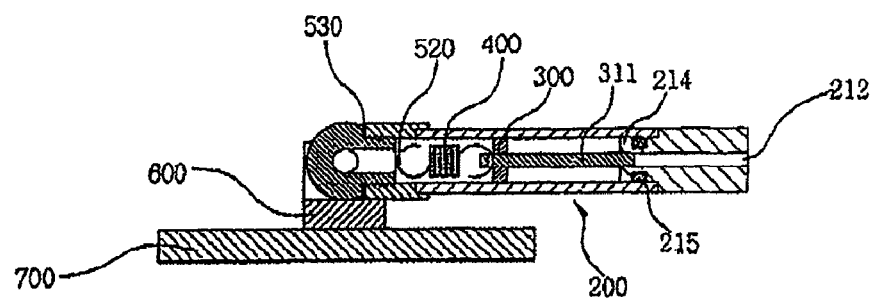
FIG. 8 is a sectional view showing the decompression valve for the sphygmomanometer according to the present invention, in which the decompression valve is rotated by 90 degrees around its longitudinal axis.

The valve body always must be upright as shown in FIG. 7. The three-way valve 500 to which valve body 200 of the present invention is connected can rotate within a range of 180 degrees in the receiving space 610. Hence, although the pedestal 700 is not placed horizontally, the three-way valve 500 is allowed for its rotation so that the valve body can be uprightly located with relation to the ground.

INDUSTRIAL APPLICABILITY

As can be seen from the foregoing, according to the present invention, the automatic decompression valve for the sphygmomanometer can gain the chance of the ideal fluid resistance using the extension spring without the friction between the valve body and the cylinder even if the valve has no the conventional decompression capability which requires the substantial skill. Thus, the decompression valve can decompress the air pressure in the cuff at a constant rate, thereby making it possible to efficiently measure the systolic pressure and the diastolic pressure. Further, since the valve body can rotate on the support, it is possible to make the valve body upright regardless of the measurement circumstance. Therefore, the measurement of the blood pressure can be efficiently performed under any circumstance. Also, there is an advantage in that the decompression valve can be horizontally folded and kept while it is not used.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. An automatic decompression valve for a sphygmomanometer using an extension spring, the valve comprising:
    a valve body, comprising a first inlet configured to receive air from a cuff, and a first outlet through which the air is exhausted;
    a piston comprising a piston shaft configured to move within the outlet in the valve body;
    a spring comprising a first end coupled to the piston;
    a three-way valve comprising a connector to which the valve body is coupled, a second inlet, and a second outlet, the three-way valve being connected to a second end of the spring; and
    a support configured to support the three-way valve;
    wherein the second end of the spring is coupled to the three-way valve by a thin plate, the thin plate being folded and inserted into the connector of the three-way valve in parallel with a direction of air flow through the connector so as to connect the spring to the three-way valve.

2. The automatic decompression valve as claimed in claim 1, wherein the valve body has a protrusion at an upper portion of the valve body, the protrusion extending into the valve body and having an air exhaust hole formed through the protrusion.

3. The automatic decompression valve as claimed in claim 1, wherein the support has supporting members that define a reception space in which the three-way valve is received.

4. The automatic decompression valve as claimed in claim 3, wherein the reception space has a diameter smaller than an outer diameter of the three-way valve.

5. The automatic decompression valve as claimed in claim 3, wherein the three-way valve is pivotally received in the reception space.

6. The automatic decompression valve as claimed in claim 1, wherein the support is connected to a pedestal.

7. The automatic decompression valve as claimed in claim 6, wherein the support and the pedestal are integrally formed.

8. The automatic decompression valve as claimed in claim 4, wherein the three-way valve is pivotally received in the reception space.

* * * * *